United States Patent
Tron

[19]

[11] Patent Number: 6,066,087

[45] Date of Patent: May 23, 2000

[54] EXERCISE BED FOR AESTHETIC AND SLIMMING TREATMENTS

[76] Inventor: Margherita Tron, Via Camaur, 17, 34100 Trieste (TS), Italy

[21] Appl. No.: 08/983,528

[22] PCT Filed: Jul. 17, 1996

[86] PCT No.: PCT/IB96/00719

§ 371 Date: Jan. 20, 1998

§ 102(e) Date: Jan. 20, 1998

[87] PCT Pub. No.: WO97/03633

PCT Pub. Date: Feb. 6, 1997

[30] Foreign Application Priority Data

Jul. 21, 1995 [IT] Italy .................................. UD95A0144

[51] Int. Cl.[7] .......................... A61G 11/00; A63B 21/00; A61H 1/00

[52] U.S. Cl. ................................ 600/21; 607/77; 601/23; 601/24

[58] Field of Search .......................... 607/81, 77; 600/21, 600/22; 482/92, 142, 148; 601/23, 24

[56] References Cited

U.S. PATENT DOCUMENTS

| | | |
|---|---|---|
| 4,565,188 | 1/1986 | Hardie ........................................ 601/23 |
| 4,671,284 | 6/1987 | Wilson et al. .............................. 601/23 |
| 4,712,538 | 12/1987 | Hardie et al. .............................. 601/23 |
| 4,884,574 | 12/1989 | Hardie et al. .............................. 601/23 |
| 5,181,289 | 1/1993 | Kassai ........................................ 5/612 |
| 5,461,739 | 10/1995 | Falbo, Sr. .................................... 5/607 |
| 5,743,050 | 4/1998 | Shibata ....................................... 52/27 |

*Primary Examiner*—Cary O'Connor
*Assistant Examiner*—Navin Natnithithadha
*Attorney, Agent, or Firm*—Adams & Wilks

[57] ABSTRACT

Bed for motor activity for aesthetic and slimming treatments, comprising at least a base (11) on which the user (14) can rest in at least a partially supine position and a cover in the shape of a dome (12) with an opening (13) associated with closing and insulating means (15), the bed having means (18, 19, 24) to carry out gymnastic and muscular exercises of the upper and/or lower limbs, there being an external control panel (17) to adjust and set the temperature, there being a first heating system comprising means (22, 23) to take in air at a controlled temperature inside the bed (10) and a second heating system comprising a plurality of lamps (27) emitting concentrated and localized rays directed towards the inside of the bed (10) and individually directed and/or able to be directed towards the body of the user (14), the combination of the action of these two distinct heating systems, together with the heat insulation created inside the bed (10), determining conditions of extreme uniformity of the temperature inside the bed (10), which temperature can be controlled for a period of time.

34 Claims, 2 Drawing Sheets

EXERCISE BED FOR AESTHETIC AND SLIMMING TREATMENTS

BACKGROUND OF THE INVENTION

1. Field of the Invention

The present invention concerns a bed for motor activity for aesthetic and slimming treatments.

In particular, the invention is applied in the field of personalized aesthetic and/or slimming treatments which can be carried out either in the appropriate specialized centers or within the home.

The invention allows the user to carry out gymnastic exercises for the movement of the upper and/or lower limbs in a closed environment which is maintained at a constant temperature higher than ambient temperature.

In particular, the bed according to the invention allows localized zones to be created inside the bed itself where the temperature is differentiated and can be differentiated according to the necessities of the specific client.

The bed according to the invention is characterised in that it is closed and thermally insulated from the outside, which makes it possible to have a constant, precise and specific differentiation of the temperatures set inside.

2. Background Information

The state of the art includes a variety of equipment and instruments for aesthetic treatments of the human body and in particular for localized slimming by means of a progressive reduction of the fatty tissues and also to correct and/or modify some irregular formations of the human body.

In this field, the method which consists of having the user do gymnastic exercises, preferably of the static type in a supine or prone position, in an environment where a physiological temperature is induced around the body, has been known for a long time.

In such machines, which are normally used in specialized centers and with the assistance of specialized staff, the user carries out a series of pre-ordained movements according to the location and the entity of the parts to be reduced.

The type of exercise and the position in which it is done, for example supine, prevent or at least considerably reduce physical fatigue and the weight on the spinal column.

In machines of this type, the consumption of energy by the user is essentially due to the movements which, even if they are gentle, activate muscles which are normally very little used, together with the greater effort made by the body to disperse heat because of the reduced heat gradient caused by the surrounding environment.

Equipment known to the state of the art however has some disadvantages because the sources of heat which it normally uses have no other function than to heat the environment in a more or less uniform and distributed way, without localizing the heat in points or areas of greater or specific interest.

In particular, in machines known to the state of the art the temperature is normally set to a value of around 37° C.; this temperature, near to the physiological temperature of the user who is doing the gymnastic activity, is considered to be the optimum temperature to achieve maximum enzyme reactivity, that is, the greatest quantity of fats burnt following the gymnastic activity.

In these machines known to the state of the art, the localization effect is achieved only by working on the muscular layers underlying the areas which have to be slimmed, however these areas all work at the same temperature, that is, the set ambient temperature.

Moreover the ambient temperature often does not correspond, throughout the period of time when the exercises are being done, to the set temperature because of the heat losses which are typical of machines known to the state of the art.

The sources of heat moreover are unable to carry out auxiliary functions connected or complementary to the slimming treatment being carried out, particularly aesthetic and/or physiotherapeutic treatments for the user's body.

Moreover, it is very difficult to adjust the heat energy radiated by the sources of heat, because of their very nature, and therefore it is difficult to personalize the heat energy according to the specific needs of the user.

What is more, using sources of heat known to the state of the art, it is not possible to heat specific parts of the body, such as the back, which therefore remains at a different temperature from the rest of the body.

Furthermore, in machines known to the state of the art, the atmosphere generally becomes stale, and there is no way to air them, for example between one client and the next.

The present applicant has considered these and other problems concerning a more rational and complete use of equipment of this type and, to overcome the shortcomings of the state of the art and to achieve further advantages, has designed, tested and embodied this invention.

SUMMARY OF THE INVENTION

This invention is set forth and characterised in the respective main claims, while the dependent claims describe variants of the main embodiment.

The purpose of this invention is to provide a bed for static motor activity for use in personalized cycles for slimming and/or aesthetic treatment.

The bed according to the invention creates a heated environment substantially insulated from the outside environment, with an opening from which only the user's head protrudes.

The opening is made of wrapping materials which make it possible to maintain the bed substantially heat insulated from the surounding environment without however causing discomfort to the user.

Substantially at the height of the hands and feet there is a plurality of instruments which make it possible for the user to do gymnastic and muscular exercises of the upper and/or lower limbs.

These instruments are typically arranged to offer resistance to the muscular effort made by the user, and are arranged and distributed along the bed in such a way that it is possible to do specific exercises which achieve a localized thinning of specific areas of the human body.

According to the invention, this resistance can be adjusted manually or also automatically.

According to a variant, there is at least one device to record the user's heart rate, associated with the gymnastic instruments.

This device continually adjusts the resistance of the gymnastic instruments according to the user's physical effort, in order to maintain the heart beat at a rate of between 55% and 90%, advantageously between 65% and 80%, of the maximum rate of the individual user.

In fact, it is in this range that motor activity allows the user to burn most of the fats and not, for example, the carbohydrates in the blood, in which case there would be no reduction in the fatty deposits.

The permitted motor activities include preferentially exercises to extend/contract the muscles by means of specific and adjustable elastic resistances and/or weights which oppose the pulling movement exercised by the user.

Other solutions include instruments for straight, circular or bicycle-type movements of the lower limbs, slope-simulators, a rowing machine for the upper limbs or other similar instruments.

According to the invention, in correspondence with at least one peripheral area of the bed, and inside the cover which defines the closed environment associated with the bed, there is an air intake system by which air is taken inside the closed environment.

The temperature of the air which is introduced is adjusted and modified during the motor activity according to the temperature desired inside the bed, for example, 37° C. approximately, in relation to other sources of heat cooperating with the inside of the bed.

The air intake system is associated with a recircling system which uses air taken from the outside so as to achieve a substantially continuous recircling of air and avoid staleness of the air.

According to the invention, inside the vault defined by the cover of the bed there is a plurality of lamps emitting concentrated heat;

The lamps can be of the incandescent type and associated with means to concentrate the flow of radiance, for example parabolic screens.

According to a solution of the invention, the lamps emit infra-red rays.

According to a variant, the direction of the lamps can be adjusted.

According to a variant, the intensity of the lamps can also be adjusted, and they can be associated with thermostats with preset functioning.

The thermostats switch on/off the lamps in the event that the temperature goes beyond the preset limits.

According to another variant, the lamps are associated with timing devices which enable them to be activated/deactivated at predefined periods.

The infra-red lamps can be fixed and directed, or are movable and can be directed, towards specific points or areas of the user's body inside the bed; they have different effects both from the aesthetic and from the therapeutic and physiotherapeutic point of view.

The synergic combination of the action of the infra-red rays on the user's body, together with the slimming action obtained from the motor activity in an environment heated to a constant temperature and set with extreme precision, gives a plurality of advantages and positive effects in aesthetic and slimming treatments.

In fact, the intake system for hot and/or cold air, together with the heat insulation created inside the bed, gives a uniform temperature, constant in the environment, except in those localized points acted upon by the infra-red lamps.

The infra-red lamps however do not create any discontinuity or sudden variations in the temperature in specific areas of the bed, given that there is the hot/cold air intake system which has the function of rebalancing and making the temperature uniform inside the bed at every moment.

The body's exposure to the infra-red rays increases the impregnation of the tissues caused by the dilatation of the blood vessels which is in turn induced by the heat, and for this reason the nutrition and oxygenization of the tissues are improved.

The increase in temperature also causes an increase in the chemical reactions and the local metabolism; a further effect is the increase in perspiration with a consequent increase in the liquids and metabolic wastes.

Moreover, the dilatation of the follicles and the softening of the layer of rough skin caused by the localized heat and the consequent increase in perspiration give a better, deeper and more intense absorbtion of any products which may have been applied on the parts exposed to the rays, such as creams, pomades, ointments etc.

This increased absorbtion also gives a more efficient use of the active ingredients contained in the products for a greater metabolic and functional efficiency of the tissues.

All this gives a greater efficiency of the applications which therefore improve and accelerate the effects of the specific treatment to slim and tone the specific parts of the human body.

By localizing the application using the infra-red lamps, it is possible to avoid the problem of heating specific areas where exposure to the heat, for contingent reasons, may be harmful.

According to a variant of the invention, the base of the bed has at least a part for the user's back which comprises means to emit heating rays, either normal or infra-red.

The function of the rays is to heat deeply the parts of the body which, supporting the weight of the body, are not heated by the hot air of the environment or the localized infra-red rays emitted by the lamps on the cover.

In particular, these rays can heat those parts of the body to a temperature which can be different both from the ambient temperature and from the surface body temperature (s) determined by the action of the infra-red rays.

According to another variant, at least the part of the bed where the user's back lies is made of transparent material which infra-red radiation emitted by lamps placed underneath the bed can pass through.

The programmed and programmable combination of the heated air intake system, the infra-red lamps and the heated back support makes it possible to obtain preordained and localized temperatures, adjustable to order and constant.

The combination of differentiated heat sources makes it possible to act on the various parts of the body alternately, in such a way as to give a pleasurable sensation of a wave of heat spreading through the body.

Moreover, in specific cases when necessary, the various parts of the body can be subjected to temperatures which are greatly different, because the sources of heat can be localized and independently adjusted.

This allows different applications and treatments to be used according to the specific and personal needs of the user.

According to another variant, the bed can be used for chromotherapy treatments, using replaceable colored lamps with varying colors according to the specific problem to be treated.

These lamps may be switched on, according to the specific treatment cycle, continually, alternately or according to preset cycles.

BRIEF DESCRIPTION OF THE DRAWINGS

The attached figures are given as a non-restrictive example and show some preferred embodiments of the invention as follows.

DETAILED DESCRIPTION OF THE PREFERRED EMBODIMENTS

Figure 1:
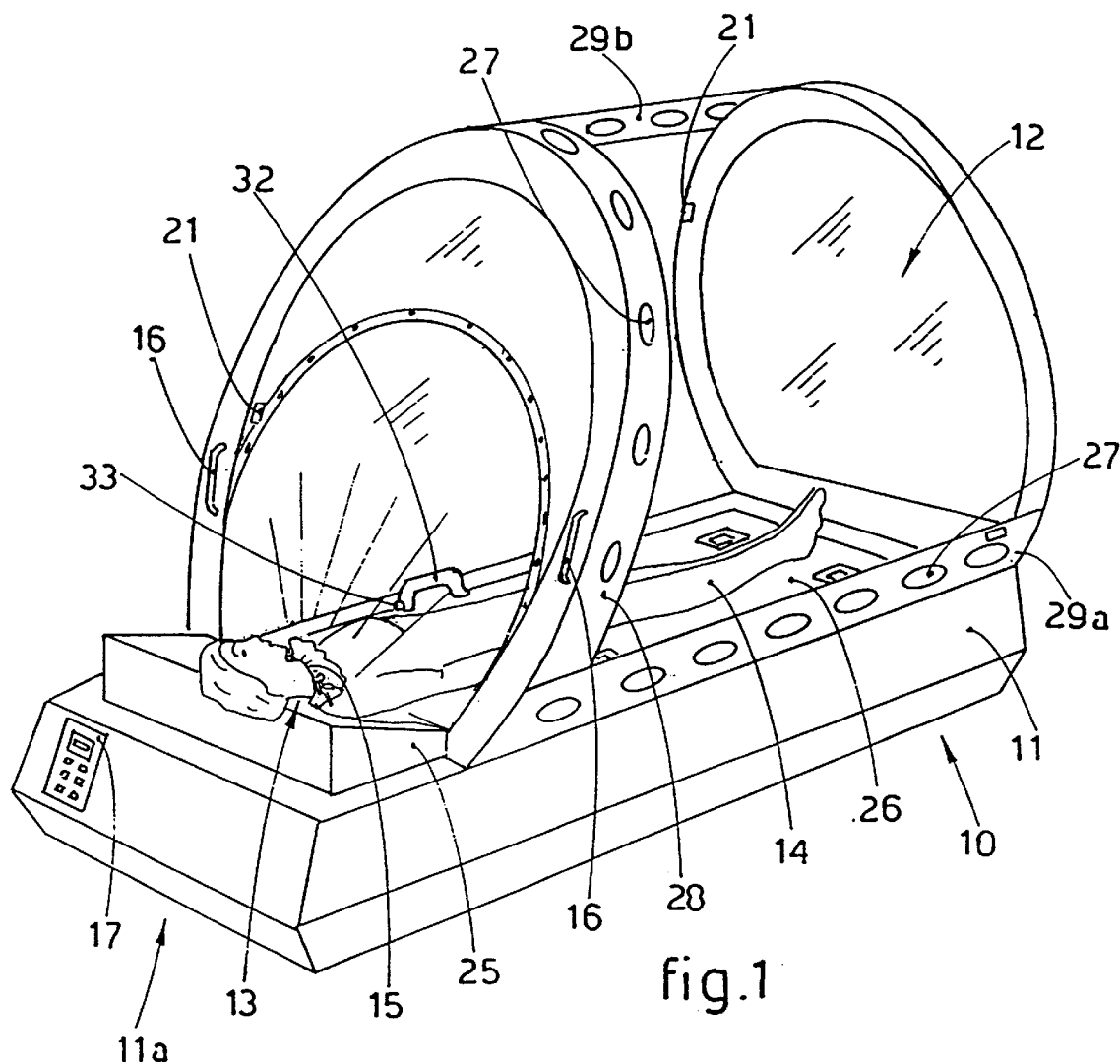
FIG. 1 shows a diagram of the bed for motor activity according to the invention.
Figure 2:
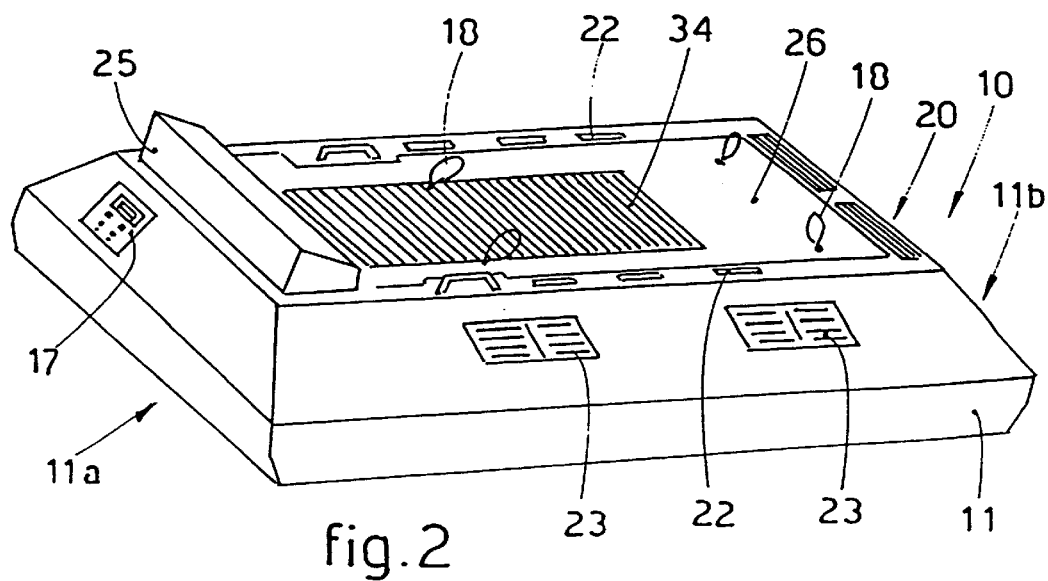
FIG. 2 shows a more detailed view of the bed in FIG. 1 without the cover.

The bed for motor activity 10 shown in FIG. 1 has a base 11 associated with a fixed, dome-shaped cover 12 made, in this case, of transparent material such as plexiglass or polycarbonate, possibly colored according to the aesthetic effect desired.

The dome 12 is closed at the rear and has at the front an opening 13 through which the user 14 can enter the inside of the bed 10.

In this case, an embodiment is shown in which the user 14 is supine during the exercises, but the bed 10 can be planned for the user 14 to do the motor activity in a vertical or subvertical position.

In a preferred embodiment of the invention, the dome 12 can be swivelled open in one direction or the other or both, to make it easier for the user 14 to enter the bed, and to allow cleaning, maintenance, replacements or otherwise on the bed 10.

The opening 13 is closed and hermetically sealed by means of a cape 15 which is substantially wrapped around the neck of the user 14 in such a way that the user's head remains outside the closed environment defined by the dome 12.

The cape 15 can moreover be closed over other parts of the body if specific parts, for example only the lower limbs, are to be treated.

The user's head rests on the pillow 25 whereas there is a mattress 26 for the body.

According to a variant not shown here, the mattress 26 is associated with a lifting system which allows it be tilted, within the limits of the dimensions of the opening 13, in such a way that particular gymnastic exercises may be carried out in a different position from the supine.

Advantageously, the front edge of the dome 12 has handles 16 which make it easier for the user 14 to enter the bed 10 and on which the user can lean during the exercises when at least part of the body is outside the bed 10.

On the front edge 11a of the base 11 there is also the control panel 17 to adjust the functional elements of the bed 10.

In this case, substantially at the height of the hands and feet of the user 14 in a prone position, the bed 10 has means to do exercises to extend and contract the muscles of the upper and lower limbs.

In particular, there are holding nooses 18 associated at the lower end, by means of cords, with elastic resistance elements 19, in this case made of spiral springs 36, which oppose the pulling force exerted by the user.

According to a variant, the elastic resistance elements 19 are made of magnetic resistance elements, or of other type, which can be adjusted manually or automatically.

Figure 4:
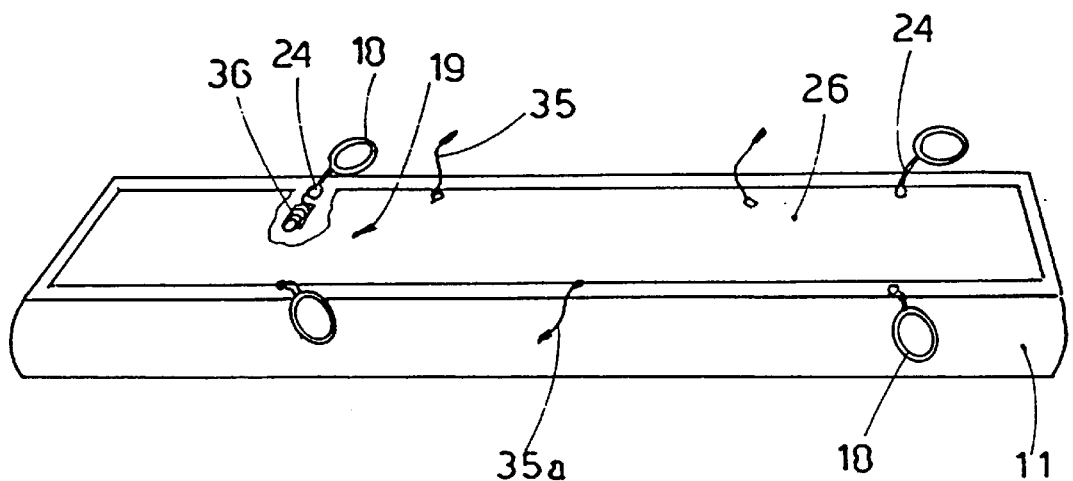
FIG. 4 shows a diagram of the side view of the bed in FIG. 1.

According to the invention, the user 14 cooperates, at least during the exercises, with a heart rate recorder, indicated by 35a in FIG. 4, which automatically sets the resistance of the elastic resistance elements 19 according to a precise heart rate being obtained by the user 14.

In particular, if during the exercise the user's heart rate under stress goes beyond the preset limits, for example between 65% and 80% of maximum beats, the intensity of the resistance opposed to the force of the elastic resistance elements 19 is varied, one way or another, until the heart rate returns within the preset limits.

The heart rate can advantageously be visualized on a display on the control panel 17, to enable the staff to follow the evolution of the effort made by the user 14 and if necessary to intervene in situations of abnormality.

The elastic resistance elements 19 are advantageously of the replaceable type so as to allow a wide range of resistances and muscular efforts to be required of the user 14.

Instead of the elastic resistance elements 19 there may be weights or other devices.

According to other embodiments of the invention, inside the bed 10 there may be instruments to carry out articulated movements and/or efforts of the limbs, advantageously adjustable in entity and/or extent according to the characteristics of the user 14 and the type of treatment to be followed.

Substantially at the height of the supine user 14, there are fixed handles 32 which help the user 14 to carry out the exercises relating to the lower limbs.

In this case, there is also an emergency button 33 so that the user 14 may signal any emergency situation.

In correspondence with the rear edge 11b of the base 11 there is a grille system 20 to take in and recircle air inside the bed 10 so that the bed 10 is aired with air taken from the outside environment.

The air intake system inside the bed 10 comprises a grille system 22 on the upper edge of the base 11 and inside the dome 12, connected with grille elements 23 which communicate with the outside.

The grille elements 22 are associated with heating elements (not shown here) which allow the air, taken from the environment by means of the grilles 23, to be heated;

The heating means can be adjusted by acting on the control panel 17 so as to define the desired temperature inside the bed 10.

Advantageously, the heating means are governed by a plurality of means 21 to measure the temperature distributed inside the bed 10 which regulate the action of the heating means according to the desired temperature being obtained and maintained in all the areas of the bed 10.

On the internal face of the dome 12, turned and directed towards localized parts of the body of the user 14, there is a plurality of lamps 27 which emit heating rays, advantageously but not necessarily infra-red rays.

Figure 3:
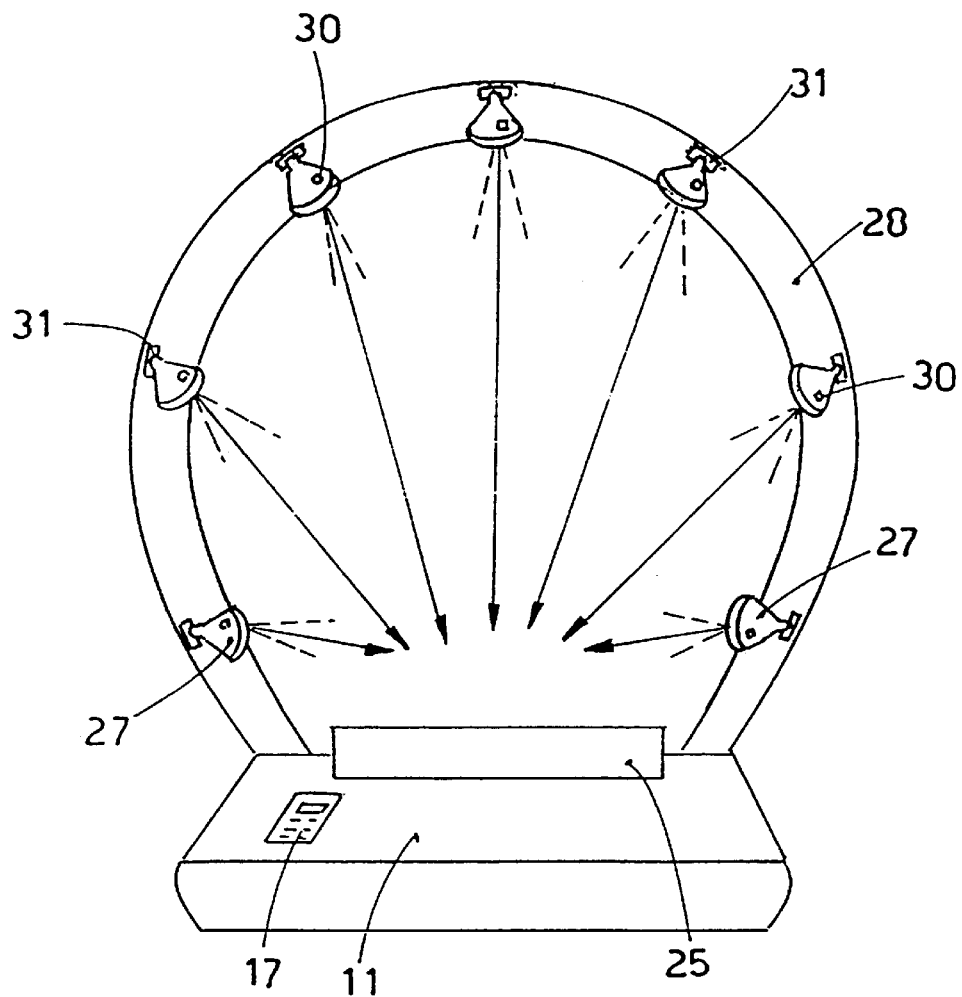
FIG. 3 shows a front view of the bed in FIG. 1;.

In a first embodiment of the invention (FIG. 3), the lamps 27 are distributed uniformly on a transverse band 28 which follows the substantially elliptic shape of the dome 12.

According to a variant, the lamps 27 are distributed on bands 29 which are lengthwise to the bed 10, below 29a or above 29b the bed 10.

These solutions may be combined or alternated, or other arrangements may be included.

The lamps 27 may be adjusted individually, both with regard to the intensity of the rays, and to the timing and to their direction, by acting on the control panel 17.

The lamps 27 are associated individually with thermostats 30 which automatically determine when they are switched on/off, and regulate the intensity of the light emitted if the temperature exceeds the preset limits.

According to a variant, the thermostats 30 are arranged near the surface of the user's body in order to regulate the functioning of the lamps 27 according to the desired temperature being obtained and maintained in correspondence with the surface areas of the body.

The lamps 27 are mounted on ball-joints 31 which allow them to be directed as desired, servoassisted with remote movement means.

According to a variant, the lamps 27 are associated with servoassisted movement systems which allow them to be moved nearer/farther from the user 14.

This positioning can be carried out both by the staff and by the user 14, according to the specific therapeutic and slimming requirements, or according to contingent situations, for example the application of creams or other on localized parts of the body, the user's build etc.

According to a variant not shown here, the lamps 27 are mounted on heads on the outside periphery of the dome 12.

According to another variant, the lamps 27 are mounted on a removable band which follows the shape of the dome 12 in order to allow them to be mounted even on beds 10 which are not specifically planned to be so used.

The direction of the lamps 27 can also be memorized in such a way as to obtain a personalized programmed position for every individual user 14 or for every category of user 14.

The lamps 27 are replaceable and can also be replaced by colored lamps for particular chemotherapy treatments.

In this case, at least a part of the mattress 26 on which the back of the user 14 rests is covered by a layer 34 provided with means to emit heating rays which strike an area which would not otherwise be affected by other sources of heat present inside the bed 10.

According to a variant not shown here, the part of the mattress 26 on which the back of the user 14 rests has at the bottom a transparent element under which there are lamps which emit heating rays.

The combination of the heat energy emitted by the intake system 22, the lamps 27 and the layer 34 makes it possible to obtain a desired distribution of the temperature inside the bed 10 and on the body of the user 14.

This distribution, according to the specific requirements, can be uniform or localized even in an accentuated way, and a differentiation in the application of the heat energy is thus assured.

The sources of heat 20, 27 and 34 can be adjusted independently and activated alternately, in such a way as to give the effect of a wave of heat which stimulates the circulation and gives the user 14 a pleasurable sensation.

According to a variant, the user 14 cooperates with a heating garment, for example a track suit with means to emit heating rays, infra-red or not, which makes it possible to obtain precise and controllable temperature values over all the body surface or over specific parts of it.

The heating garment is associated with the control panel 17 to regulate the temperature induced by the individual heating elements present in it.

In this case, there are also temperature sensors 35 which can be associated with the body of the user and which give signals to the system which regulates the sources of heat 20, 27 and 34, together with means which measure the ambient temperature 21, in order to adjust and if necessary disactivate the sources of heat 20, 27 and 34.

What is claimed is:

1. A bed for motor activity for aesthetic and slimming treatments, the bed comprising:
    a base;
    body support means disposed over the base for supporting the body of a user when the user is at least in a partially supine position;
    a cushion disposed over the base for cushioning the head of the user;
    a cover connected to the base for covering the body of the user except for the user's head, the cover having a generally dome shape defining an interior space of the bed, at least one transverse band, and an opening for providing access into the interior space of the bed;
    closing and insulating means for closing the opening of the cover and insulating the interior space of the bed;
    exercising means for carrying out gymnastic and muscular exercises of upper and/or lower limbs of the user's body, the exercising means having adjusting means for adjusting a resistance to a pulling action exerted by the user during the gymnastic and muscular exercises;
    an external control panel for adjusting and setting a temperature in the interior space of the bed;
    a first heating and temperature maintaining system for heating and maintaining the interior space of the bed at a temperature which is substantially uniform and substantially equal to that of the user's body, the first heating and temperature maintaining system having air intake means disposed on the base exteriorly of the cover for taking in air, inlet means disposed on a side of the base within the interior space of the bed and in fluid communication with the air intake means for admitting the air into the interior space at a controlled temperature, and circulating means for circulating the air in the interior space of the bed;
    a second heating system comprised of a plurality of lamps at least some of which are disposed on the transverse band of the cover for emitting heating rays toward localized areas of the user's body; and
    a third heating system disposed over the body support means for heating at least a lower part of the user's body supported by the body support means.

2. A bed as claimed in claim 1, wherein the cover has at least one longitudinal band disposed on an upper median part of the cover; and
    wherein at least some of the lamps of the second heating system are disposed on the longitudinal band of the cover.

3. A bed as claimed in claim 2, wherein at least some of the lamps of the second heating system are disposed longitudinally along a lower median part of the cover.

4. A bed as claimed in claim 1, wherein at least some of the lamps of the second heating system are disposed longitudinally along a lower median part of the cover.

5. A bed as claimed in claim 1, wherein the first heating and temperature maintaining system has monitoring means for monitoring the temperature in the interior space of the bed and for controlling at least the second heating system.

6. A bed as claimed in claim 1, wherein at least some of the lamps of the second heating system comprise infrared lamps.

7. A bed as claimed in claim 1, wherein at least some of the lamps of the second heating system comprise incandescent lamps; and
    further comprising means for reflecting and concentrating the heat rays emitted by the lamps of the second heating system.

8. A bed as claimed in claim 1, further comprising a plurality of thermostats each associated with a respective lamp of the second heating system for controlling and regulating the temperature of the rays emitted by the lamp.

9. A bed as claimed in claim 8, further comprising a plurality of mounting members each for mounting a respective lamp of the second heating system to the cover;

wherein each of the thermostats is mounted on a respective mounting member.

10. A bed as claimed in claim 9, further comprising switching means for switching ON/OFF at least some of the lamps of the second heating system.

11. A bed as claimed in claim 8, wherein the thermostats are mounted on the bed in positions proximate the user's body during use of the bed.

12. A bed as claimed in claim 1, wherein at least some of the lamps of the second heating system are colored.

13. A bed as claimed in claim 1, further comprising monitoring means for monitoring the heart rate of the user; and wherein the adjusting means adjusts the resistance exerted by the user during the gymnastic and muscular exercises in accordance with an output from the monitoring means to maintain the heart rate of the user within a range of 55% to 90% of a maximum heart rate permitted for the user.

14. A bed as claimed in claim 13, wherein the adjusting means adjusts the resistance exerted by the user during the gymnastic and muscular exercises in accordance with an output from the monitoring means to maintain the heart rate of the user within a range of 65% to 80% of the maximum heart rate permitted for the user.

15. A bed as claimed in claim 14, wherein the external control panel has a display member for displaying the heart rate of the user at least while the user performs the gymnastic and muscular exercises.

16. A bed as claimed in claim 13, wherein the external control panel has a display member for displaying the heart rate of the user at least while the user performs the gymnastic and muscular exercises.

17. A bed as claimed in claim 1, further comprising an emergency distress button for alerting of an emergency distress during use of the bed.

18. A bed as claimed in claim 1, further comprising a plurality of ball joints each for connecting a respective lamp of the second heating system to the cover, and positioning means for positioning the ball joints by servoassisted remote control.

19. A bed as claimed in claim 1, wherein at least a portion of the body support means is made of a transparent material through which heat radiation is permitted to pass; and further comprising a plurality of heat sources disposed in the base for emitting heat radiation through the transparent portion of the body support means.

20. A bed as claimed in claim 1, wherein the exercise means includes means for performing articulated exercises of lower and/or upper limbs of the user's body.

21. A bed for motor activity for aesthetic and slimming treatments, the bed comprising:

a base for supporting a user's body;

a cover disposed over the base to define an interior space of the bed, the cover having an opening for providing access by the user into the interior space;

closing means for closing the opening of the cover to hermetically seal the interior space of the bed;

exercise means for carrying out gymnastic and muscular exercises;

an external control panel for adjusting and setting a temperature in the interior space of the bed;

a first heating system for directing air into the interior space of the bed at a controlled temperature;

and a second heating system comprised of a plurality of lamps for emitting heat rays towards the body of the user in the interior space of the bed.

22. A bed as claimed in claim 21, wherein the cover has a generally dome shape.

23. A bed as claimed in claim 21, wherein the cover has at least one transverse band; and wherein at least some of the lamps are disposed on the transverse band of the cover.

24. A bed as claimed in claim 21, wherein the cover has at least one longitudinal band;

and wherein at least some of the lamps are disposed on the longitudinal band of the cover.

25. A bed as claimed in claim 21, wherein the lamps comprise incandescent lamps.

26. A bed as claimed in claim 21, wherein the lamps comprise infrared lamps.

27. A bed as claimed in claim 21, wherein the external control panel includes means for varying and presetting an intensity of the heat rays emitted by the lamps.

28. A bed as claimed in claim 21, further comprising a plurality of thermostats each associated with a respective lamp for controlling and regulating the temperature of the emitted rays.

29. A bed for motor activity for aesthetic and slimming treatments, the bed comprising:

a base having a support surface for supporting the body of a user;

a cover disposed over the base to define an interior space of the bed, the cover having an opening for providing access by the user into the interior space;

a hermetic seal member for closing the opening to hermetically seal the interior space of the bed;

a first heating system for heating the interior space of the bed and maintaining the interior space at a temperature substantially equal to that of the user's body;

and a second heating system for emitting heat rays toward the user's body in the interior space of the bed.

30. A bed as claimed in claim 29, further comprising at least one exercising device for exercising the user's body during use of the bed.

31. A bed as claimed in claim 29, further comprising a third heating system disposed on the support surface of the base for heating at least a part of the user's body supported by the support surface.

32. A bed as claimed in claim 29, further comprising a support member disposed on a portion of the base outside the interior space of the bed for supporting the head of the user.

33. A bed as claimed in claim 29, wherein the first heating system comprises air intake means disposed on the base exteriorly of the cover for taking in air, inlet means disposed on a side of the base within the interior space of the bed and in fluid communication with the air intake means for admitting the air into the interior space at a controlled temperature, and circulating means for circulating the air in the interior space of the bed.

34. A bed as claimed in claim 29, wherein the second heating system comprises a plurality of lamps.

* * * * *